US 6,685,934 B1

(12) United States Patent
Mallet et al.

(10) Patent No.: US 6,685,934 B1
(45) Date of Patent: *Feb. 3, 2004

(54) RECOMBINANT ADENOVIRUSES CODING FOR BASIC FIBROBLAST GROWTH FACTORS (BFGF)

(75) Inventors: Jacques Mallet, Paris (FR); Michel Perricaudet, Ecrosnes (FR); Emmanuelle Vigne, Ivry sur Seine (FR); Frédéric Revah, Paris (FR); Marc Abitbol, Paris (FR); Paul Roustan, Les Ulis (FR)

(73) Assignee: Aventis Pharma S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,482
(22) PCT Filed: Mar. 24, 1995
(86) PCT No.: PCT/FR95/00374
  § 371 (c)(1),
  (2), (4) Date: Oct. 9, 1996
(87) PCT Pub. No.: WO95/26409
  PCT Pub. Date: Oct. 5, 1995

(30) Foreign Application Priority Data

Mar. 29, 1994 (FR) ............................. 94 03682

(51) Int. Cl.[7] ................. A01N 63/00; C12N 7/00; C12N 5/00
(52) U.S. Cl. ................. 424/93.1; 435/325; 435/235.1
(58) Field of Search .................. 435/320.1, 325, 435/366, 395, 397, 399, 398, 235.1; 514/44; 424/93.1

(56) References Cited

U.S. PATENT DOCUMENTS 5,439,818 A  *  8/1995  Fiddes et al. ............ 435/240.2

FOREIGN PATENT DOCUMENTS

| EP | 0 293 090 | * 11/1988 | |
| EP | 0582796 A1 | * 5/1993 | ........... C12N/15/95 |
| FR | 2 688 514 | 3/1992 | |
| WO | WO 93/08828 | 11/1992 | |
| WO | WO 94/08026 | 9/1993 | |
| WO | WO 94/20146 | 2/1994 | |
| WO | WO 94/11506 | 5/1994 | |

OTHER PUBLICATIONS

Caillaud et al. Adenoviral vector as a gene delivery system into cultured rat neuronal and glial cells. European Journal of Neuroscience, vol. 5, No. 10, pp. 1287–1291, Oct. 1, 1993.*
La Salle et al. An adenovirus vector for gene transfer into neurons and glia in the brain. Science, vol. 259, No. 5097, pp. 988–990, Feb. 12, 1993.*
Friedman, T. Gene therapy for neurological disorders. Trends in Genetics, vol. 10, No. 6, pp. 210–214, Jun. 1994.*
NIH panel, Report and Recommendations of the Panel to assess the NIH investment in Research on Gene Therapy, Dec. 7, 1995.*

(List continued on next page.)

Primary Examiner—Deborah J. Reynolds
Assistant Examiner—Joseph Woitach
(74) Attorney, Agent, or Firm—Finnegan, Henderson, Farabow, Garrett & Dunner LLP

(57) ABSTRACT

Recombinant adenoviruses comprising a heterologous DNA sequence coding for basic blast growth factors (bFGF), preparation and uses thereof for the treatment and/or prevention of neurodegenerative diseases.

21 Claims, 1 Drawing Sheet

OTHER PUBLICATIONS

Figure 1:
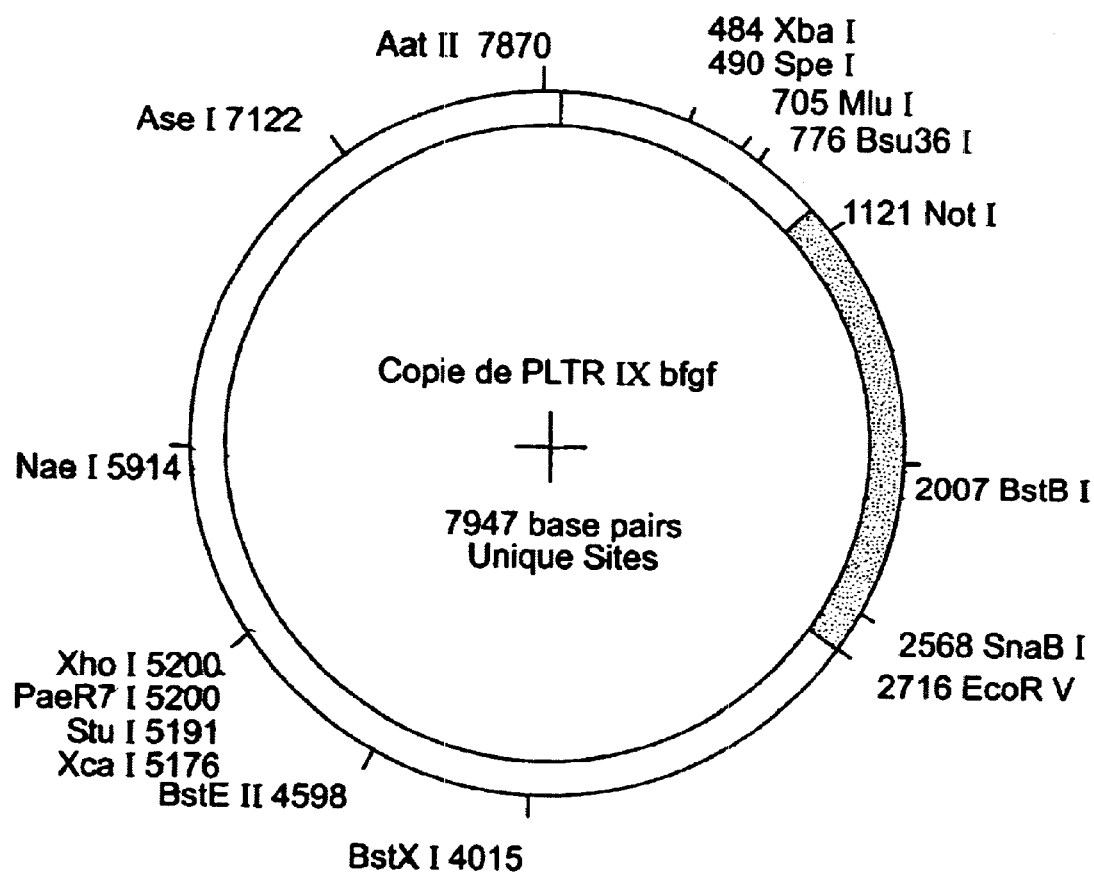

Investigative Ophthalmology & Visual Science, 34, 3, (1993), Bok, Retinal Transplantation and Gene Therapy Present Realities and Future Possibilities.

Science, vol. 259, 988–990, (1993), Le Gal La Salle Robert Berrard Ridoux StratfordPerricaude et al., An Adenovirus Vector for Gene Transfer into Neurons and Glia in the Brain.

Congress of the French Society of Hematology, 35 (3), 299–300, (1993), Peschanski Lisovoski Akli Caillaud Wahrman et al., Gene Transfer for Therapeutic Purposes in the Central Nervous System.

NeuroReport, 5, 7, 801–804 (1994), Ridoux Robert Zhang Perricaudet Mallet La Gal La Salle, The Use of Adenovirus Vectors for Intracerebral Grafting of Transfected Nervous Cells.

FEBS Lett., 208(2), 211–225, (1992), Roemer Friedmann, Concepts and Strategies for Human Gene Therapy.

Medicine/Sciences, 9, 2, 208–210, (1993), Danos Moullier Heard, Reimplantation de cellules genetiquement modifiees dans des neo–organes vascularises.

Brain Research, 648, 1, 171–175, (1994) Ridoux Robert Zhang Perricaudet Mallet Le Gal La Salle, Adenoviral Vectors as Functional Retrograde Neuronal Tracers.

Science, 256, 5063, 1550–1552, (1992), Culver Ram Wallbridge Ishii Oldfield Blaese, In Vivo Gene Transfer with Retroviral Vector–Producer Cells for Treatment of Experimental Brain Tumors.

\* cited by examiner

RECOMBINANT ADENOVIRUSES CODING FOR BASIC FIBROBLAST GROWTH FACTORS (BFGF)

The present invention relates to recombinant adenoviruses which encompass a DNA sequence encoding the basic fibroblast growth factors. The invention also relates to the preparation of these vectors, to the pharmaceutical compositions containing them, and to their therapeutic use, in particular in gene therapy for treating and/or preventing neurodegenerative diseases.

The increase in length of life in western countries is accompanied by a steady growth in neurodegenerative diseases such as Alzheimer's disease, Parkinson's disease, Huntington's chorea, amyotrophic lateral sclerosis, etc. Thus Parkinson's disease, for example, affects 4% of people over the age of 65, and Alzheimer's disease affects 10% of those over the age of 70 and 30% of those over the age of 80. Generally speaking, all these diseases result from a progressive loss of neuronal cells in the central nervous system, or even within very localized structures as in the case of Parkinson's disease.

During recent years, numerous research projects have been developed with a view to understanding the mechanisms of this degeneration associated with ageing, in order to be able to develop means of treatment, and also means of prevention, using gene therapy.

The trophic factors are a class of molecules possessing properties which stimulate axonal growth or survival of nerve cells. The first factor possessing neurotrophic properties, i.e. NGF ("nerve growth factor"), was characterized some forty years ago (for review, see Levi-Montalcini and Angelleti, Physiol. Rev. 48 (1968) 534). Other neurotrophic factors have been identified, in particular the fibroblast growth factors (FGFs). The fibroblast growth factors (FGFs), the acidic and basic forms of which have been identified, are subjected to retrograde transport in several neuronal populations, including the nigrostriatal system (Fergusson and Johnson, 1991 J. Comp. Neurol. 313:693), and enable dopaminergic neurones of the mesencephalon to survive in vitro (Knusel et al, 1990, J. Neurosci. 10, 558). The main forms of human bFGFs possess molecular weights of 22.5 kd, 21 kd and 18 kd, respectively. (Prats H., Kagahd M., Parts A. C., Klagsbrun M., Lelias J. M., Liauzun P., Chalon P., Tauber J. P., Amalric F., Smith J. A. and Caput D., Proc. Natl. Acad. Sci. U.S.A. 86, 1836–1840 (1989)).

In their basic form, human fibroblast growth factors (bFGFs) are, in particular, recommended for preventing and/or treating hereditary or acquired retinopathies which are of a degenerative nature. Similarly, they are able to restore normal photoreceptor morphology.

For this purpose, bFGFs are usually injected directly by the intravitreous or subretinal route at the site to be treated. However, this form of administration is not completely satisfactory. Thus, in view of the tumorigenic character of bFGFs, it is important to ensure that they are essentially localised in the desired region of the body. When they are injected by a general route, it is not possible to be certain of preventing the bFGFs from diffusing into the blood circulation.

The particular object of the present invention is to propose a particularly advantageous solution to this problem.

The present invention relates to the development of particularly efficient vectors for delivering, in vivo and in a localized manner, therapeutically active quantities of bFGF, thereby enabling undesirable side-effects to be avoided.

The present invention is particularly advantageous for administering bFGF as a therapeutic agent.

More precisely, the present invention is directed towards developing particularly efficient vectors for delivering, in vivo and in a localized manner, therapeutically active quantities of the specific gene encoding bFGF into the nervous system.

In Application No. PCT/EP93/02519, which is pending concomitantly, it was demonstrated that it was possible to employ adenoviruses as vectors for transferring a foreign gene into the nervous system in vivo, and for expressing the corresponding protein.

More specifically, the present invention relates to novel constructs which are particularly suitable and efficient for transferring basic fibroblast growth factors (bFGFs).

More precisely, it relates to a recombinant adenovirus which encompasses a DNA sequence encoding bFGF or one of its derivatives, to its preparation and to its use for treating and/or preventing neurodegenerative diseases.

Thus, the Applicant has demonstrated that it is possible to construct recombinant adenoviruses which contain a sequence encoding bFGF, and to administer these recombinant adenoviruses in vivo, and that this administration makes it possible to achieve stable and localized expression of therapeutically active quantities of bFGF in vivo in the nervous system, in particular for the treatment of retinopathies, with no cytopathic effect.

An initial subject of the invention is, therefore, a defective recombinant adenovirus which encompasses at least one DNA sequence encoding all, or an active part, of basic fibroblast growth factor (bFGF) or of one of its derivatives.

The basic fibroblast growth factor (bFGF) which is produced within the scope of the present invention can be human bFGF or an animal bFGF. In particular, it can be rat bFGF.

The DNA sequence which encodes bFGF, and which is used within the scope of the present invention, can be a cDNA, a genomic DNA (gDNA), or a hybrid construct consisting, for example, of a cDNA in which one or more introns are inserted. The sequences involved can also be synthetic sequences or semisynthetic sequences.

Particularly advantageously, a cDNA or a gDNA is employed.

According to one preferred embodiment of the invention, the sequence is a gDNA sequence encoding bFGF. When this sequence is used, it is possible to achieve improved expression in human cells.

Naturally, prior to its incorporation into an adenovirus vector according to the invention, the DNA sequence is advantageously modified, for example by means of site-directed mutagenesis, particularly for the purpose of inserting appropriate restriction sites, because the sequences described in the prior art are not constructed to be used in accordance with the invention, and prior adaptations may prove to be necessary in order to obtain substantial levels of expression.

Within the meaning of the present invention, a derivative of bFGF is understood to mean any sequence which is obtained by modification and which encodes a product which retains at least one of the biological properties of bFGF (trophic effect and/or differentiating effect). Modification is understood to mean any mutation, substitution, deletion, addition or modification of a genetic and/or chemical nature. These modifications can be carried out using the techniques known to a person skilled in the art (see general molecular biological techniques below). Within the meaning of the invention, the derivatives can also be obtained by hybridization from nucleic acid libraries, using the native sequence or a fragment thereof as the probe.

These derivatives are, in particular, molecules which have a great affinity for their sites of attachment, sequences which result in improved expression in vivo, molecules which are more resistant to proteases, and molecules which have a greater therapeutic efficacy or side-effects which are less marked, or, perhaps, novel biological properties.

Those preferred derivatives which may more specifically be cited are natural variants, molecules in which one or more residues have been replaced, derivatives which have been obtained by deleting regions which are not involved, or are only involved to a limited extent, in interaction with the binding sites under consideration, or which express an undesirable activity, and derivatives which, as compared with the native sequence, include additional residues, such as, for example, a secretory signal and/or a junction peptide.

According to one favoured embodiment of the invention, the DNA sequence encoding bFGF or one of its derivatives also includes a secretory signal which enables the synthesized bFGF to be directed into the secretory paths of the infected cells. In this way, the synthesized bFGF is advantageously released into the extra-cellular compartments and can thus activate its receptors. However, the signal can also be a heterologous secretory signal or even an artificial secretory signal. To the extent that this is possible, the secretory signal is advantageously the native signal belonging to bFGF. This will, in particular, be the case for rat bFGF, which has its own peptide signal. On the other hand, human bFGF does not have such a signal.

The DNA sequence which encodes the whole, or part, of the bFGF or of one of its derivatives can also be an antisense sequence whose expression in the target cell enables expression of the bFGF to be regulated. Preferably, the heterologous DNA sequence comprises a gene encoding an antisense RNA which is able to regulate translation of the bFGF mRNA. The antisense sequence can be the whole, or only a part, of the DNA sequence encoding bFGF, with this sequence being inserted in the inverse orientation in the vector according to the invention.

Advantageously, the sequence encoding bFGF is placed under the control of signals which enable it to be expressed in nerve cells, including, in particular, the retinal cells. Preferably, these signals are heterologous expression signals, that is signals which are different from those which are naturally responsible for expressing bFGF. They can, in particular, be sequences which are responsible for expressing other proteins, or synthetic sequences. In particular, they can be promoter sequences from eucaryotic or viral genes. For example, they can be promoter sequences which are derived from the genome of the cell which it is wished to infect. Similarly, they can be promoter sequences from the genome of a virus, including the adenovirus which is employed. The promoters E1A, MLP, CMV and RSV LTR, etc., may, for example, be cited in this respect. Furthermore, these expression sequences can be modified by the addition of activating or regulatory sequences, or sequences which permit tissue-specific expression. Thus, it can be particularly useful to employ expression signals which are specifically, or in the main, active in nerve cells, such that the DNA sequence is only expressed, and only produces its effect, when the virus has actually infected a nerve cell. Examples of promoters which may be cited in this respect are the promoters of neuron-specific enolase, of GFAP, and, more especially, those of rhodopsin and of tyrosinase.

In a first specific embodiment, the invention relates to a defective recombinant adenovirus which encompasses a cDNA sequence encoding human basic fibroblast growth factor (hbFGF) under the control of the RSV LTR promoter.

The invention also relates to a defective recombinant adenovirus which encompasses a cDNA sequence encoding human basic fibroblast growth factor (bFGF) under the control of the rhodopsin promoter or the tyrosinase promoter, as well as to a defective recombinant adenovirus which encompasses a cDNA sequence encoding rat basic fibroblast growth factor (bFGF) under the control of the rhodopsin promoter or the tyrosinase promoter.

In another specific embodiment, the invention relates to a defective recombinant adenovirus which comprises a gDNA sequence encoding basic fibroblast growth factor (bFGF) under the control of the RSV LTR promoter.

Thus, the Applicant has demonstrated that use of the LTR promoter of Rous sarcoma virus (RSV) enabled bFGF to be expressed over a long period and at a substantial level in cells of the nervous system, in particular the central nervous system.

Still in a preferred embodiment, the invention relates to a defective recombinant adenovirus which encompasses a DNA sequence encoding neurotrophic factor bFGF under the control of a promoter which enables it to be expressed mainly in the nervous system.

A particularly preferred embodiment for implementing the present invention consists of a defective recombinant adenovirus which encompasses ITR sequences, an encapsidation sequence, and a DNA sequence encoding basic fibroblast growth factor (bFGF), or a derivative thereof, under the control of a promoter enabling expression to take place in the main in the nervous system, and in which the E1 gene and at least one of the genes E2, E4 and L1–L5 is non-functional.

The defective adenoviruses according to the invention are adenoviruses which are incapable of replicating autonomously in the target cell. In general, the genome of the defective adenoviruses which are employed within the scope of the present invention therefore lacks at least one of the sequences which are necessary for replication of the said virus in the infected cell. These regions can be eliminated (in whole or in part), or rendered non-functional, or replaced by other sequences, in particular by the DNA sequence encoding bFGF.

Preferably, the defective virus of the invention retains the sequences of its genome which are necessary for encapsidating the viral particles. Still more preferably, as indicated above, the genome of the defective recombinant virus according to the invention encompasses ITR sequences, an encapsidation sequence, the non-functional E1 gene, and a non-functional version of at least one of the genes E2, E4 and L1–L5.

Different serotypes of adenovirus exist, whose structures and properties vary to some degree. Of these serotypes, preference is given, within the scope of the present invention, to the use of type 2 or type 5 human adenovirus (Ad 2 or Ad 5) or adenoviruses of animal origin (see application FR 93 05954). Those adenoviruses of animal origin which can be employed within the scope of the present invention and which may be cited are adenoviruses of canine, bovine, murine (e.g. Mavl, Beard et al., Virology 75 (1990) 81), ovine, porcine, avian and also simian (e.g. SAV) origin. Preferably, the adenovirus of animal origin is a canine adenovirus, more preferably a CAV2 adenovirus [Manhattan or A26/61 (ATCC VR-800) strain for example]. Preferably, adenoviruses of human or canine origin, or a mixture thereof, are employed within the scope of the invention.

The defective recombinant adenoviruses according to the invention may be prepared by any technique known to the person skilled in the art (Levrero et al., Gene 101 (1991) 195, EP 185 573; Graham, EMBO J. 3 (1984) 2917). In particular, they can be prepared by homologous recombination between an adenovirus and a plasmid which carries, inter alia, the DNA sequence encoding bFGF. The homologous recombination takes place following cotransfection of the said adenovirus and plasmid into an appropriate cell line. The cell line which is used should preferably (i) be transformable by the said elements, and (ii), include sequences which are able to complement the defective adenovirus genome part and which are preferably in an integrated form in order to avoid any risk of recombination. As an example of a cell line, mention may be made of the human embryonic kidney cell line 293 (Graham et al., J. Gen. Virol. 36 (1977) 59), which, in particular, contains, integrated into its genome, the left-hand part of the genome of an Ad5 adenovirus (12%). Strategies for constructing vectors derived from adenoviruses have also been described in applications nos. FR 93 05954 and FR 93 08596, which are incorporated herein by reference.

Subsequently, the adenoviruses which have multiplied are recovered and purified using standard molecular biological techniques, as illustrated in the examples.

The particularly advantageous properties of the vectors of the invention ensue, in particular, from the construct employed (defective adenovirus, in which certain viral regions are deleted), from the promoter used for expressing the sequence encoding bFGF (preferably viral or tissue-specific promoter), and from the methods of administering the said vector, resulting in an expression of the bFGF which is efficient and which takes place in the appropriate tissues. The present invention thus supplies viral vectors which can be used directly in gene therapy, and which are particularly well suited to and efficient for directing the expression of bFGF in vivo. The present invention thus offers a novel approach which is particularly advantageous for treating and/or preventing neurodegenerative diseases.

The present invention also relates to any use of an adenovirus as described above for preparing a pharmaceutical composition which is intended for the treatment and/or prevention of neurodegenerative diseases. More specifically, it relates to any use of these adenoviruses for preparing a pharmaceutical composition which is intended for the treatment and/or prevention of Parkinson's disease, Alzheimer's disease, amyotrophic lateral sclerosis (ALS), Huntington's disease, epilepsy, vascular dementia, and also retinopathies.

The retinopathies can, more specifically, be any central or peripheral retinal degeneration, or a mixture of these, as well as any retinopathy which is or is not acquired, in particular diabetic retinopathies.

The present invention also relates to a pharmaceutical composition which includes one or more defective recombinant adenoviruses as previously described. These pharmaceutical compositions can be formulated with a view to administering them by the topical, oral, parenteral, intranasal, intravenous, intramuscular, subcutaneous, intraocular or transdermal, etc., route. Preferably, the pharmaceutical compositions of the invention contain an excipient which is pharmaceutically acceptable for an injectable formulation, in particular for an injection which takes place directly into the nervous system of the patient. These compositions can, in particular, be sterile, isotonic solutions, or dry, in particular lyophilized, compositions which, as a result of sterile water or physiological saline, as the case may be, being added to them, enable injectable solutions to be made up. Direct injection into the nervous system of the patient is advantageous since it enables the therapeutic effect to be concentrated in the affected tissues. Direct injection into the central nervous system of the patient is advantageously carried out using a stereotactic injection apparatus. The reason for this is that the site of injection can be targeted with a high degree of precision using such an apparatus.

In this respect, the invention also relates to a method for treating neurodegenerative diseases, which method comprises administering a recombinant adenovirus as defined above to a patient. More specifically, the invention relates to a method for treating neurodegenerative diseases, which method comprises the stereotactic administration of a recombinant adenovirus as defined above.

The doses of defective recombinant adenovirus which are employed for the injection can be adjusted in dependence on different parameters, in particular in dependence on the mode of administration employed, on the pathology concerned and also on the desired duration of the treatment. Generally speaking, the recombinant adenoviruses according to the invention are formulated and administered in the form of doses containing between $10^4$ and $10^{14}$ pfu/ml, preferably from $10^6$ to $10^{10}$ pfu/ml. The term pfu ("plaque-forming unit") corresponds to the infective power of a virus solution, and is determined by infecting an appropriate cell culture and then measuring, in general after 48 hours, the number of plaques of infected cells. The techniques for determining the pfu titre of a viral solution are well documented in the literature.

The invention also relates to any mammalian cell which is infected with one or more defective recombinant adenoviruses as described above. More specifically, the invention relates to any population of human cells which is infected with these adenoviruses. The cells can, in particular, be fibroblasts, myoblasts, hepatocytes, keratinocytes, endothelial cells, glial cells, etc.

The cells according to the invention can be derived from primary cultures. They can be removed by any technique known to the person skilled in the art and then cultured under conditions which enable them to proliferate. Fibroblasts, more specifically, can be readily obtained from biopsies, for example using the technique described by Ham [Methods Cell. Biol. 21a (1980) 255]. These cells can be employed directly for infection with adenoviruses, or preserved, for example by freezing, in order to establish autologous banks with a view to subsequent use. The cells according to the invention can also be secondary cultures which are obtained, for example, from previously established banks.

Cells in culture are then infected with recombinant adenoviruses in order to confer on the cells the ability to produce bFGF. The infection is carried out in vitro using techniques known to the person skilled in the art. The person skilled in the art can adjust the multiplicity of infection and, where appropriate, the number of infection cycles which are carried out, in accordance with, in particular, the type of cells used and the desired number of virus copies per cell. Naturally, these steps should be effected under appropriate conditions of sterility where it is intended to administer the cells in vivo. The person skilled in the art can adjust the doses of recombinant adenovirus which are used for infecting the cells in accordance with the desired objective. The conditions described above for in vivo administration can be applied to in vitro infection.

The present invention also relates to a pharmaceutical composition which includes an adequate quantity of defective recombinant virus as previously described.

According to one favoured embodiment of the invention, these compositions are very particularly suitable for use in treating retinopathies.

In particular, the defective recombinant virus can be in the form of an injectable solution, eye drops, an ophthalmic ointment, etc. The pharmaceutically acceptable excipients for such formulations which are suitable for ocular usage are, in particular, saline solutions (monosodium phosphate, disodium phosphate, sodium chloride, potassium chloride, calcium chloride or magnesium chloride, etc., or mixtures of such salts), petroleum jelly, liquid paraffin, etc.

Naturally, the therapeutic applications of eye drops or ophthalmic ointments may be more limited owing to lower diffusion of the defective recombinant virus.

In their use for treating ocular pathologies, the defective recombinant viruses according to the invention can be administered in different ways, in particular by means of single or multiple subretinal injections, preceded if appropriate by vitrectomy, or intravitreous injections. Subretinal injection can be carried out selectively in different compartments of the eye; in particular, the injection can be made into the vitreous body, the anterior chamber or the retrobulbar space. These different modes of injection enable the different tissues of the eye, in particular the corneal endothelium, the photoreceptor cells, the bipolar cells, the ganglion cells or the cells of the oculomotor muscles, to be infected in a targeted manner.

The invention also relates to an implant which comprises mammalian cells which are infected with one or more defective recombinant adenoviruses as described above, and to an extracellular matrix. Preferably, the implants according to the invention contain from $10^5$ to $10^{10}$ cells. More preferably, they contain from $10^6$ to $10^8$.

More specifically, the extracellular matrix in the implants of the invention comprises a gel-forming compound and, where appropriate, a support for anchoring the cells.

Various types of gel-forming compounds can be employed for preparing implants according to the invention. The gel-forming compounds are used in order to enclose the cells in a matrix having the constitution of a gel, and in order to promote anchorage of these cells to the support, if need be. Various agents for adhering cells can, therefore, be used as gel-forming agents, such as, in particular, collagen, gelatine, glycosaminoglycans, fibronectin, lectins, etc. Collagen is preferably used within the scope of the present invention. This collagen can be of human, bovine or murine origin. More preferably, type I collagen is used.

As indicated above, the compositions according to the invention advantageously include a support for anchoring the cells. The term anchoring denotes any form of biological and/or chemical and/or physical interaction which leads to adhesion and/or fixation of the cells to the support. Otherwise, the cells can cover the support which is employed and/or penetrate into the interior of the support. Within the scope of the invention, preference is given to employing a solid, non-toxic and/or biocompatible support. In particular, use can be made of polytetrafluoroethylene (PTFE) fibres or of a support of biological origin.

The implants according to the invention can be implanted at different sites in the body. In particular, the implantation can be effected in the peritoneal cavity, in subcutaneous tissue (suprapubic region, iliac or inguinal fossae, etc.), in an organ, a muscle, a tumour, the central nervous system, and also under a mucous membrane. The implants according to the invention are particularly advantageous in that they enable the release of the therapeutic product within the body to be regulated: in the first place, this release is determined by the multiplicity of infection and by the number of implanted cells. After that, the release can be regulated either by withdrawal of the implant, which definitively stops the treatment, or by using regulatable expression systems which enable the expression of therapeutic genes to be induced or repressed.

The present invention thus offers a very efficient means of treating or preventing neurodegenerative diseases such as Alzheimer's, Parkinson's, and Huntington's diseases, and ALS as well as retinopathies. Furthermore, the adenoviral vectors according to the invention exhibit important advantages which are associated, in particular, with their very high degree of efficiency in infecting nerve cells, thereby making it possible to achieve infections using low volumes of viral suspension. Furthermore, infection with the adenoviruses of the invention is highly localized to the site of injection, thereby avoiding the risk of diffusion into adjacent cerebral structures.

Furthermore, this treatment can be applied both to humans and to any animal such as sheep, cattle, rodents, domestic animals (dogs, cats, etc.), horses, fish, etc.

The present invention will be described in more detail with the aid of the following examples, which should be regarded as illustrative and not limiting.

FIGURE LEGEND

FIG. 1: Depiction of the vector pLTR IX-hbFGF.

GENERAL MOECULAR BIOLOGICAL TECHNIQUES

The standard methods employed in molecular biology, such as preparative extractions of plasmid DNA, centrifugation of plasmid DNA in a caesium chloride gradient, electrophoresis on agarose or acrylamide gels, purification of DNA fragments by electroelution, extraction of proteins with phenol or with phenol/chloroform, precipitation of DNA in a saline medium using ethanol or isopropanol, transformation into *Escherichia coli*, etc., are well known to the person skilled in the art and widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

Plasmids such as pBR322 and pUC and phages of the M13 series are of commercial origin (Bethesda Research Laboratories).

For the ligations, the DNA fragments can be separated according to size by electrophoresis on agarose or acrylamide gels, extracted with phenol or with a phenol/chloroform mixture, precipitated using ethanol, and then incubated in the presence of phage T4 DNA ligase (Biolabs) according to the supplier's recommendations.

The protruding 5' ends can be filled in using the Klenow fragment of *E. coli* DNA polymerase I (Biolabs) according to the suppier's specifications. The protruding 3' ends are destroyed in the presence of phage T4 DNA polymerase (Biolabs) which is used in accordance with the manufacturer's recommendations. The protruding 5' ends are destroyed by careful treatment with S1 nuclease.

In vitro site-directed mutogenesis using synthetic oligodeoxynucleotides can be performed in accordance with the method developed by Taylor et al. [Nucleic Acids Res. 13 (1985) 8749–8764] using the kit distributed by Amersham.

Enzymic amplification of DNA fragments by the technique termed PCR [Polymerase-catalyzed Chain Reaction, Saiki R. K. et al., Science 230 (1985) 1350–1354; Mullis K. B. and Faloona F. A., Meth. Enzym. 155 (1987) 335–350] can be carried out using a DNA thermal cycler (Perkin Elmer Cetus) according to the manufacturer's specification.

Nucleotide sequences can be verified by the method developed by Sanger et al. [Proc. Natl. Acad. Sci. USA, 74 (1977) 5463–5467] using the kit distributed by Amersham.

EXAMPLES

Example 1

Construction of the Vector pLTR IX-rbFGF

This example describes the construction of a vector which encompasses a DNA sequence encoding rat bFGF under the control of a promoter consisting of the RSV LTR.

1.1. Starting Vector (pLTR IX): Vector pLTR IX contains, in particular, the left-hand region of the AdS adenovirus encompassing the ITR and the encapsidation site, the LTR promoter of RSV, and a region of the AdS adenovirus proceeding from the pIX gene to the EagI restriction site, enabling homologous recombination to take place in vivo. This vector has been described by Stratford-Perricaudet et al. (J. Clin. Invest. 90 (1992) 626).

1.2 Construction of a cDNA Sequence Encoding rbFGF.

For producing vectors according to the invention, a cDNA sequence encoding rat bFGF is constructed as follows:

A fragment of 820 base pairs containing the sequence encoding rat bFGF and its own peptide signal was isolated from the plasmid pUC13-bFGF by digesting it with the enzyme EcoRI. This fragment was then subcloned into the corresponding site of the Bluescript (Pharmacia) vector.

1.3 Construction of the Vector pLTR IX-rbFGF

This example describes the construction of the vector pLTR IX-bFGF which contains the sequence encoding rat bFGF (Shimasaki S., Emoto N;, Koba A., Mercado M., Shibata F., Cooksey K., Baird A. and Lin N. Complementary DNA cloning and sequencing of the rat ovarian basic fibroblasts growth factor and tissue distribution study of its mRNA, B.B.R.C. 157, 256–263, 1988) under the control of the LTR of the RSV virus, as well as Ad5 adenovirus sequences which enable recombination to take place in vivo.

The DraII-SacII fragment was isolated by enzymic digestion from the construct prepared in example 1.2. This fragment contains the sequence encoding the bFGF. This fragment was isolated and purified by electrophoresis on an LMP (low melting point) agarose gel, and then treated with T4 DNA polymerase in order to render it blunt-ended. This fragment was subsequently inserted into the EcoRV site of vector pLTR IX (example 1.1.) in order to generate vector PLTR IX-rbFGF. The whole of the nucleotide sequence of the rbFGF insert was then verified by dideoxynucleotide sequencing.

Example 2

Construction of the Vector pLTR IX-hbFGF.

This example describes the construction of a vector which encompasses a DNA sequence encoding human bFGF under the control of a promoter consisting of the RSV LTR.

A fragment of 1.63 kb, encoding human bFGF, was isolated from the plasmid pSCT40 by enzymic digestion at the XhoI and EcoRV sites. This fragment was then inserted at the SalI (1028) and EcoRV (1119) sites of vector PLTR IX (example 1.1.) in order to generate vector pLTR IX-hbFGF (FIG. 1). The whole of the nucleotide sequence of the bFGF insert was subsequently verified by dideoxynucleotide sequencing.

Example 3

Construction of Recombinant Adenoviruses Containing a Sequence Encoding Human BFGF Vector pLTR IX-bFGF was linearized and cotransfected together with a deficient adenoviral vector into helper cells (cell line 293) which supplied the functions encoded by the adenovirus E1 regions (E1A and E1B) in trans.

More precisely, the adenovirus Ad-bFGF was obtained by in vivo homologous recombination between the mutant adenovirus Ad-dl1324 (Thimmappaya et al., Cell 31 (1982) 54) and vector pLTR IX-bFGF, according to the following protocol: plasmid pLTR IX-bFGF and adenovirus Ad-dl1324, linearized with the enzyme ClaI, were cotransfected into cell line 293 in the presence of calcium phosphate, in order to enable homologous recombination to take place. The recombinant adenoviruses which were generated in this way were selected by plaque purification. Following isolation, the DNA of the recombinant adenovirus was amplified in cell line 293, resulting in a culture supernatant which contained unpurified defective recombinant adenovirus possessing a titre of approximately $10^{10}$ pfu/ml.

The viral particles are subsequently purified by gradient centrifugation.

What is claimed is:

1. An implant comprising an isolated human cell and an extracellular matrix wherein the cell is infected with at least one defective recombinant adenovirus comprising at least one DNA sequence encoding all or an active part of basic fibroblast growth factor, and wherein said cell is a retinal cell, glial cell, or nerve cell.

2. The implant according to claim 1, wherein the extracellular matrix comprises a gel-forming compound.

3. The implant according to claim 2, wherein the gel-forming compound is selected from the group consisting of collagen, gelatine, glucosaminoglycans, fibronectin and lectins.

4. The implant according to claim 2, wherein the extracellular matrix further comprises a support for anchoring the infected cells.

5. The implant according to claim 4, wherein the support comprises polytetrafluoroethylene fibres.

6. The implant according to claim 1, wherein the at least one DNA sequence encoding all or an active part of basic fibroblast growth factor is operably linked to a promoter or enhancer that specifically, or in the main, controls expression in nerve or glial cells.

7. The implant according to claim 6, wherein the signal is a viral promoter.

8. The implant according to claim 6, wherein the signal is selected from the group consisting of a neuron-specific enolase promoter, a GFAP promoter, a rhodopsin promoter and a tyrosinase promoter.

9. The implant according to claim 6, comprising a cDNA sequence encoding human basic fibroblast growth factor operably linked to a rhodopsin promoter or a tyrosinase promoter.

10. The implant according to claim 6, comprising a cDNA sequence encoding rat basic fibroblast growth factor operably linked to a rhodopsin promoter or a tyrosinase promoter.

11. The implant according to claim 1, wherein the adenovirus lacks regions of its genome necessary to replication in a target cell.

12. The implant according to claim 11, wherein the adenovirus lacks ITRs and an encapsidation sequence, and wherein the E1 gene and at least one of the E2, E4, and L1–L5 genes are non-functional.

13. The implant according to claim 11, wherein said adenovirus is a human type Ad 2 or Ad 5 or a canine type CAV-2.

14. The implant according to claim 1, wherein the at least one DNA sequence is a cDNA sequence.

15. The implant according to claim 1, wherein the at least one DNA sequence is a gDNA sequence.

16. The implant according to claim 1, wherein the at least one DNA sequence encodes human basic fibroblast growth factor.

17. The implant according to claim 1, wherein the at least one DNA sequence encodes rat basic fibroblast growth factor.

18. The implant according to claim 1, wherein the defective recombinant adenovirus comprises at least one first DNA sequence complementary to a second DNA sequence encoding all or an active part of basic fibroblast growth factor, wherein the first DNA sequence is operably linked to a promoter or enhancer that specifically, or in the main, controls expression in nerve or glial cells and is an antisense sequence regulating expression of the basic fibroblast growth factor gene.

19. The implant according to claim 18, wherein the antisense sequence is an RNA regulating translation of the basic fibroblast growth factor mRNA.

20. The implant according to claim 1, wherein the cell is a mammalian cell.

21. The implant according to claim 1, wherein said cell is a human cell.

* * * * *